United States Patent [19]
Cummins

[11] Patent Number: 5,910,304
[45] Date of Patent: *Jun. 8, 1999

[54] LOW-DOSE ORAL ADMINISTRATION OF INTERFERONS

[75] Inventor: Joseph M. Cummins, Amarillo, Tex.

[73] Assignee: Texas A&M University System, College Station, Tex.

[*] Notice: This patent is subject to a terminal disclaimer.

[21] Appl. No.: 07/875,630

[22] Filed: Apr. 28, 1992

Related U.S. Application Data

[63] Continuation of application No. 07/044,317, Apr. 30, 1987, abandoned, which is a continuation of application No. 06/688,868, Jan. 4, 1985, Pat. No. 4,820,515, which is a continuation-in-part of application No. 06/448,951, Dec. 13, 1982, Pat. No. 4,497,795.

[51] Int. Cl.⁶ .................................................. A61K 38/21
[52] U.S. Cl. ........................ 424/85.7; 424/85.4; 424/85.5; 424/85.6
[58] Field of Search .................................. 424/85.4, 85.5, 424/85.6, 85.7

[56] References Cited

U.S. PATENT DOCUMENTS

| | | |
|---|---|---|
| 3,536,809 | 10/1970 | Applezweig . |
| 3,906,092 | 9/1975 | Hillerman et al. . |
| 3,972,995 | 8/1976 | Tsuk et al. . |
| 4,053,582 | 10/1977 | Stickl . |
| 4,226,848 | 10/1980 | Nagai et al. . |
| 4,250,163 | 2/1981 | Nagai et al. . |
| 4,273,703 | 6/1981 | Osther et al. . |
| 4,276,282 | 6/1981 | Sugimoto et al. . |
| 4,460,574 | 7/1984 | Yabrov . |
| 4,462,985 | 7/1984 | Cummins, Jr. . |
| 4,497,795 | 2/1985 | Cummins . |
| 4,572,832 | 2/1986 | Kigasawa et al. . |
| 4,605,555 | 8/1986 | Sato et al. . |
| 4,649,075 | 3/1987 | Jost . |
| 4,675,184 | 6/1987 | Hasegawa et al. . |
| 4,699,136 | 10/1987 | Krauser . |
| 4,710,191 | 12/1987 | Kwiatek et al. . |
| 4,713,239 | 12/1987 | Babaian et al. . |
| 4,746,508 | 5/1988 | Carey et al. . |
| 4,764,378 | 8/1988 | Keith et al. . |
| 4,803,072 | 2/1989 | Dalton et al. . |
| 4,820,515 | 4/1989 | Cummins .............................. 424/85.7 |
| 4,828,830 | 5/1989 | Wong . |
| 5,830,456 | 11/1998 | Cummins .............................. 424/85.7 |

FOREIGN PATENT DOCUMENTS

| | | |
|---|---|---|
| 4841285 | 4/1986 | Australia . |
| 0 107 498 | 5/1984 | European Pat. Off. . |
| 0 177 342 | 4/1986 | European Pat. Off. . |
| 0 180 737 | 5/1986 | European Pat. Off. . |
| PCT/US81/01103 | 8/1981 | WIPO . |
| PCT/DK82/00092 | 10/1982 | WIPO . |

OTHER PUBLICATIONS

Toneva, V., *Bulletin de l'Office International des Epizooties*, vol. 88, 1977, pp. 631–637 (Summary).
Rodder, H., Thuman, D., Thuman, E., *Tierarztliche Umschau*, vol. 34, No. 10, 1979, pp. 720–724 (Summary).
"In Vivo and Clinical Studies," Norman B. Finter & Robert K. Oldham, eds., *Interferon*, vol. 4, 1985, pp. 137, 148, 173, 218, 226, 284, 285, 330.
*Chemical Abstracts*, vol. 67, 1967, p. 7536 [80070u], "Effect of Interferon on the Antibody Formation in Chicks with Pseudopest," Litvinov, A.N.
"Time and Dosage Dependence of Immunoenhancement by Murine Type II Interferon Preparations", Sonnenfeld et al., *Cellular Immunology*, 40, 1978, pp. 285–293.
"Interferons and Their Actions", W.E. Stewart II and A.A. Gotlieb, eds., 1977, pp. 102–104.
"Antiviral Effect of Bacterially Produced Human Interferon (Hu–IFNa$_2$) Against Experimental Vaccinia Infection in Calves", *Journal of Interferon Research*, 5:129–126, 1985, Werenne, J. et al.
"Effect of Human Leukocyte A Interferon on Prevention of Infectious Bovine Rhinotracheitis Virus Infection of Cattle", Roney, C.S. et al., *Am. J. Vet. Res.*, vol. 46, No. 6, Jun. 1985, pp. 1251–1255.
"Response of Feline Leukemia Virus–Induced Nonregenerative Anemia to Oral Administration of an Interferon–Containing Preparation", *Feline Practice*, vol. 12, No. 3, No. 3, May–Jun. 1982, pp. 6–15, Tompkins, M.B. and Cummins, J.
"Interferon Enters The Fray", *Farm Journal*, Oct. 1985, pp. 12–13, Miller, B.
"Interferon as an Adjuvant for Hepatitis B Vaccination in Non– and Low–Responder Populations", Grob, P.J. et al., *Eur. J. Clin. Microbiol.*, Jun. 1984, vol. 3, No. 3, pp. 195–198.
"Protection of Calves Against Rhinovirus Infection by Nasal Secretion Interferon Induced by Infectious Bovine Rhinotracheitis Virus", *American Journal of Veterinary Research*, Cummins, J.M. and Rosenquist, B.D., Feb., 1980, vol. 41, No. 2, pp. 161–165.
"Bovine Respiratory Disease—A Symposium", R.W. Loan, ed., Texas A&M University Press, College Station, TX, 1984 pp. 484–485.
"Activity of Exogenous Interferon In The Human Nasal Mucosa", *Texas Reports on Biology and Medicine*, vol. 35, 1977, Greenberg, S.B., et al., pp. 491–496.
"Inhibition of Respiratory Virus Infection by Locally Applied Interferon", Merigan, T.C., et al., *The Lancet*, Mar. 17, 1973, pp. 563–567.

(List continued on next page.)

*Primary Examiner*—David L. Fitzgerald
*Attorney, Agent, or Firm*—Barnes & Thornburg

[57] ABSTRACT

Improved methods for administering an interferon (IFN) to a warm-blooded vertebrate are described. The methods employ oral administration of the IFN to the vertebrate in very low dosages, for example, 0.1 to 1.5 IU per pound of body eight per dose.

8 Claims, No Drawings

OTHER PUBLICATIONS

"Trials of Interferon in Respiratory Infections of Man", Tyrrell, D.A.J., *Texas Reports on Biology and Medicine*, vol. 35, 1977, pp. 486–490.

"Bacteria–Derived Human Leukocyte Interferons After in Vitro Humoral and Cellular Immune Responses", Shalaby, M.R. and Weck, P.K., *Cellular Immunology*, 82, 1983, pp. 269–281.

"Clinical and Laboratory Investigations on Man: Systemic Administration of Potent Interferon to Man", Strander, H., et al., *J. Natl. Cancer Inst.*, 51: 733–742, 1973.

"Application of Human Leukocyte Interferon in Severe Cases of Virus B Hepatitis", Vlatkovic, R., et al., *Proc. Symposium on Interferon 1979*, Yugoslav Academy of Sciences and Arts, Zagreb, pp. 173–183.

"Effect of Interferon on Vaccination in Volunteers", *The Lancet*, Apr. 28, 1962, pp. 873–875 (Report to Medical Research Council from the Scientific Committee on Interferon).

"Induction of Ocular Resistance to Vaccinia Virus by Typhoid Vaccine: Role of Interferon", Oh, J.O. and Yoneda, C., *The Journal of Immunology*, vol. 102, No. 1, 1969, pp. 145–154.

"Clinical Trials With Exogenous Interferon: Summary of a Meeting", *The Journal of Infectious Diseases*, vol. 139, No. 1, Jan. 1979, pp. 109–123.

"Some Results and Prospects in the Study of Endogenous and Exogenous Interferon", *The Interferons, An International Symposium*, Soloviev, V.D., Geo. Rita, ed., Academic Press, 1968, pp. 233–243.

"Influenza and Interferon Research in the Soviet Union—Jan. 1973", *The Journal of Infectious Diseases*, vol. 128, No. 2, Aug. 1973, pp. 261–264.

"The Results of Controlled Observations on the Prophylaxis of Influenza with Interferon", Solov'ev, V.D., *World Health Organization*, 1949, 41, 683–688.

"Children's Respiratory Viral Diseases Treated With Interferon Aerosol", Jia–xiong, D., et al., *Chinese Medical Journal*, 100(2): 162–166, 1987.

*Essential Clinical Virology*, R.G. Sommerville, Blackwell Scientific Publications, pp. 154–157.

"Comparative Intranasal Pharmacokinetics of Interferon Using Two Spray Systems", Davies, H.W. et al., *J. Interferon Research*, 1983, pp. 443–449.

"The Common Cold: Control?", Couch, R.B., *The Journal of Infectious Diseases*, vol. 150, No. 2, Aug. 1984, pp. 167–173.

*Principles and Practice of Infectious Diseases*, 2nd ed., Mandell, G.L., Douglas, R.G. Jr., Bennett, J.E., eds., A. Wiley Medical publication, pp. 85–96, 863, 968.

*Antiviral Agents and Viral Diseases of Man*, edited by G.J. Galasso, T.C. Merigan, R.A. Buchanan, Raven Press, New York, 1979, pp. 407–408, 430–431.

*Antiviral Agents and Viral Diseases of Man*, 2nd ed., edited by G.J. Galasso, T.C. Merigan, R.A. Buchanan, Raven Press, New York, 1979, pp. 407–408, 430–431.

"Interferon Perspective", Information on Interferon provided in 1981 by the International Preventative Medicine Foundation, Melbourne FL, Ronald Jones, Vice President.

American Interhealth, Melbourne Beach, Florida, Production Information.

Biovet International, Inc., Canine and Feline Interferons, 1981 Product Description and Label.

"Agriferon®–C", Immuno Modulators Laboratories, Inc., Stafford, Texas, Lymphokine Preparation for prophylactic treatment of infectious bovine rhinotracheitis virus associated with shipping fever—for cattle use in Texas only, product brochure.

"Agriferon®–C" A bold new approach to managing shipping fever in cattle. Immuno Modulators Laboratories, Inc., Stafford, Texas, product advertisement.

"Equiferon" A totally new approach to viral respiratory infection in horses, Immuno Modulators Laboratories, Inc., Stafford, Texas, product advertisement.

"Pet Interferon Alpha", Amarillo Cell Culture Company, Inc., Amarillo, Texas, Lymphokine Preparation for treatment of feline leukemia virus and canine parvovirus diseases, product brochure.

Texas Department of Health Application for License, Amarillo Cell Culture Company, Inc., for Human Interferon Alpha, (Alpha Interferon) as Pet Interferon, May 6, 1985.

"Circulating Interferon in Rabbits After Administration of Human Interferon by Different Routes", Cantel, K. and Ryhala, L., *Journal of General Virology*, 1973, 20, pp. 97–104.

"Pharmacokinetics of Recombinant Alpha A Interferon Following IV Infusion and Bolus, IM, and PO Administrations to African Green Monkeys", Wills, R.J., et al., *Journal of Interferon Research*, vol. 4, No. 3, 1984, pp. 399–409.

"Pharmacokinetics of Recombinant Leukocyte A Interferon Following Various Routes and Modes of Administration to the Dog", Gibson, D.M., et al., *Journal of Interferon Research*, 5:403–408 (1985).

"Stimulation of Humoral Immunity by Interferon", *III Mediterranean Congress of Chemotherapy*, Smerdel, S., et al., Sep. 21–24, 1982 presentation, vol. 2, p. 132, Oct. 1983.

"Interferon Preparations as Modifiers of Immune Responses", Braun, W., Levy, H.B., *Proc. Soc. Exp. Biol. Med.*, vol. 141, pp. 769–773, 1972.

"Interferon and the Immune System: A Review (Limited to Alpha and Beta Interferons)", De Maeyer, Edward, *The Biology of the Interferon System*, pp. 203–209, Elsevier/North–Holland Biomedical Press, 1981.

"Effect of Virus–Induced Interferon on the Antibody Response of Suckling and Adult Mice", Vignauz, F., et al., *Eur. J. Immunol.*, vol. 10, pp. 767–772, 1980.

"The Clinical Use of Human Leukocyte Interferon in Viral Infections", Ikic, D., et al., *International Journal of Clinical Pharmacology, Therapy and Toxicology*, vol. 19, No. 11, pp. 498–505, 1981.

"Primjena Humanog Leukocitnog Interferona U Male Djece Sa Gingivostomatitisom", Salaj–Rakic, T., et al., *Proceedings—Yugoslav–Pediatric Congress*, Sarayevo, 1979, p. 730.

"Colorectal Administration of Human Interferon–Alpha", Bocci, et al., *International Journal of Pharmaceutics*, vol. 24, pp. 109–114, 1985.

"Interferon Administered Orally: Protection of Neonatal Mice From Lethal Virus Challenge", Schafer, T., et al., *Science*, Jun. 23, 1972, vol. 176, pp. 1326–1327.

"Erste Erfahrungen bei der Behandlung von Virusbedington Kalberdurchfallen mit Genetechnisch Erzeugtem Interferon", Hofmann, V.W., et al., *Dtsch. tierarztl. Wschr.*, vol. 92, pp. 278–280.

"Treatment and Prevention of Acute Respiratory Virus Infections in Children With Leukocytic Interferon", Arnaoudova, V., *Rev. Roum Med.—Virol.*, 1976, 27, pp. 83–88.

"Administration of Human Leukocyte Interferon in Herpes Zoster. I. Safety, Circulating Antiviral Activity, and Host Responses to Infection", G.W. Jordan et al., *The Journal of Infectious Diseases*, vol. 130, No. 1, Jul. 1974, pp. 56–62.

"The Preventive Effect of Human Interferon–Alpha Preparation on Upper Respiratory Disease", J. Imanishi et al., *Journal of Interferon Research*, vol. 1, No. 1, 1980, pp. 169–178.

"Effect of Radix Astragali Seu Hedysari On The Interferon System", H. Yunde et al., *Chinese Medical Journal*, 94(1):35–40, 1981.

"Effect of Low Dosage of Interferon on Natural Killer Activity in Patients with HBsAg–Positive Chronic Active Hepatitis", N. Matsumura, et al., *Digestion*, 30: 195–199, 1984.

"Effects of Interferon Preparations on Rabbit Corneal Xenograft", J. Imanishi, et al., *Archives of Virology*, 53, 157–161 (1977).

"Prevention From Naturally Acquired Viral Respiratory Infection By Interferon Nasal Spray", H. Saito, et al., *Rhinology*, 23, 291–295, 1985.

LOW-DOSE ORAL ADMINISTRATION OF INTERFERONS

This is a continuation of application Ser. No. 07/044,317 filed Apr. 30, 1987 (now abandoned), which is a continuation of application Ser. No. 06/688,868 filed Jan. 4, 1985 (now U.S. Pat. No. 4,820,515 issued Apr. 11, 1989), which is a continuation-in-part of application Ser. No. 06/448,951 filed Dec. 13, 1982 (now U.S. Pat. No. 4,497,795 issued Feb. 5, 1985).

BACKGROUND OF THE INVENTION

This invention relates generally to a novel method of using interferon in low dosages to regulate appetite and efficiency of food utilization in warm-blooded vertebrates. This invention also relates to the novel use of interferon in low dosages to prevent and treat bovine respiratory disease complex.

"Interferon" is a term generically comprehending a group of vertebrate glycoproteins and proteins which are known to have various biological activities, such as antiviral, antiproliferative, and immunomodulatory activity in the species of animal from which such substances are derived. The following definition for interferon has been accepted by an international committee assembled to devise a system for the orderly nomenclature of interferons: "To qualify as an interferon a factor must be a protein which exerts virus nonspecific, antiviral activity at least in homologous cells through cellular metabolic processes involving synthesis of both RNA and protein." *Journal of Interferon Research*, 1, pp. vi (1980).

Since the first descriptions of interferon by Isaacs and Lindeman [see, *Proc, Roy, Soc. London* (Ser. B), Vol. 147, pp. 258 et sea. (1957) and U.S. Pat. No. 3,699,222], interferon has been the subject of intensive research on a worldwide basis. Publications abound concerning the synthesis of interferon; M. Wilkinson and A. G. Morris, Interferon and the Immune System 1: Induction of Interferon by Stimulation of the Immune System, Interferons: From Molecular Biology to Clinical Application, Eds: D. C. Burke and A. G. Morris, Cambridge Univ. Press, 1983, pp. 149–179; P. I. Marcus, Chapter 10, Interferon Induction by Virus, Interferons and Their Applications, Eds: P. E. Came and W. A. Carter, Springer Verlag, (Handbook of Experimental Pharmacology V. 71) 1984, pp. 205–232; its proposed molecular characterizations; P. B. Sehgal, How Many Human Interferons Are There?. Interferon 1982, Ed: I. Gresser, Academic Press, 1982, pp. 1–22; J. Collins, Structure and Expression of the Human Interferon Genes, Interferons: From Molecular Biology to Clinical Application, Eds: D. C. Burke and A. G. Morris, Cambridge Univ. Press, 1983, pp. 35–65; K. C. Zoon and R. Wetzel, Chapter 5, Comparative Structures of Mammalian Interferons, 1a: Interferons and Their Applications, Eds: P. E. Came and W. A. Carter, Springer Verlag, (Handbook of Experimental Pharmacology V. 71) 1984, pp. 79–100; its clinical applications; M. Krim, Chapter 1, Interferons and Their Applications: Past, Present, and Future, Interferons and Their Applications, Eds: P. E. Came and W. A. Carter, Springer Verlag, (Handbook of Experimental Pharmacology V. 71) 1984; S. B. Greenberg and M. W. Harmon, Chapter 21, Clinical Use of Interferons: Localized Applications in Viral Diseases, Ibid. pp. 433–453; and proposed mechanisms of its antitumor, antiviral, and immune system activities. G. M. Scott, The Antiviral Effects of Interferon, From Molecular Biology to Clinical Application, Eds: D. C. Burke and A. G. Morris, Cambridge Univ. Press, 1983, pp. 279–311; M. McMahon and I. M. Kerr, The Biochemistry of the Antiviral State, Ibid. pp. 89–108; J. S. Malpas, The Antitumor Effects of Interferon, Ibid. pp. 313–327; J. Taylor-Papadimitrion, The Effects of Interferon on the Growth and Function of Normal and Malignant Cells, Ibid. pp. 109–147.

Because of the intensity and disparate origins of research concerning interferon and its characteristics and uses, there exists a substantial lack of uniformity in such matters as classification of interferon types. There are also numerous, sometimes contradictory, theories concerning the mode of action of interferon in producing clinical effects. The following brief summary of the current state of knowledge regarding interferon will aid in understanding the present invention.

Although originally isolated from cells of avian origin (chick allantoic cells), interferon production has been observed in cells of all classes of vertebrates, including mammals, amphibians, and reptiles. Interferon production by vertebrate cells is seldom spontaneous but is often readily "induced" by treatment of cells (in vivo or in vitro) with a variety of substances including viruses, nucleic acids (including those of viral origin as well as synthetic polynucleotides), lipopolysaccharides, and various antigens and mitogens.

Interferons have generally been named in terms of the species of animal cells producing the substance (e.g., human, murine, or bovine), the type of cell involved (e.g., leukocyte, lymphoblastoid, fibroblast) and, occasionally, the type of inducing material responsible for interferon production (e.g., virus, immune). Interferon has been loosely classified by some researchers according to induction mode as either Type I or Type II, with the former classification comprehending viral and nucleic acid induced interferon and the latter class including the material produced as a lymphokine through induction by antigens and mitogens. More recently, the international committee devising an orderly nomenclature system for interferon has classified interferon into types on the basis of antigenic specificities. In this newer classification, the designations alpha ($\alpha$), beta ($\beta$), and gamma ($\gamma$) have been used to correspond to previous designations of leukocyte, fibroblast, and type II (immune) interferons, respectively. Alpha and beta interferons are usually acid-stable and correspond to what have been called type I interferons; gamma interferons are usually acid-labile and correspond to what has been called type II interferons. The international committee's nomenclature recommendations apply only to human and murine interferons. *Journal of Interferon Research*, 1 pp. vi (1980).

Determination of precise molecular structures for interferon was for some time beyond the capacities of the art. In the years since interferon was first characterized as proteinaceous on grounds of its inactivation by trypsin, attempts to purify and uniquely characterize were frustrated by its high specific activity as well as its apparent heterogeneity. Presently, some precision in determining molecular structure has been achieved for interferon. See P. B. Sehgal, supra,; J. Collins, supra; and K. C. Zoon and R. Wetzel, supra.

In its earliest applications, interferon was employed exclusively as an antiviral agent and the most successful clinical therapeutic applications to date have been in the treatment of viral or virus-related disease states. It became apparent, however, that exogenous interferon was sometimes capable of effecting regression or remission of various metastatic diseases. An overview of current clinical trials of interferon as an antiviral and antiproliferative therapeutic agent through early 1983 is contained in The Biology of the Interferon System 1983, Proceedings of the Second International TNO Meeting on the Biology of the Interferon System, Rotterdam, The Netherlands, Apr. 18–22, 1983, and Antiviral Research, Mar. 1983, Special Abstract Issue, Elsevier/North-Holland Biomedical Press, Netherlands.

The clinical agent of choice in this work has been human leukocyte interferon, "mass-produced" by procedures involving collection and purification of vast quantities of human buffy coat leukocytes, induction with virus, and isolation from culture media. The need for interferon of human source is, of course, consistent with the longstanding conclusion that interferon is "species specific," i.e., biologically active, in vivo, only in species homologous to the source cells.

In the work described above, interferon has been administered parenterally, i.e., intramuscularly and intradermally, with some successful topical and intranasal usages having been reported. It has seldom been administered intravenously because of substantial adverse effects attributable to "contaminants" in crude and even highly purified isolates. The invention of applicant described in U.S. Pat. No. 4,462,985, and in PCT International Application No. PCT/US 81/01103, filed Aug. 18, 1981, published Mar. 4, 1982 as WO 82/00588, the disclosures of which are hereby incorporated by reference, concerns the use of interferon of heterologous species origin, and also involves oral administration of interferon. Prior to these disclosures, there had been no reports of therapeutically successful oral administration of interferon. This circumstance was consistent with the widely held belief that interferon would not withstand exposure to a digestive environment such as that found in mammals.

In addition to use in antiviral and antitumor therapy, interferon has rather recently been noted to possess immunomodulatory effects, both immunopotentiating and immunosuppressive in nature. B. Lebleu and J. Content, Mechanisms of Interferon Action: Biochemical and Genetic Approaches, Interferon 1982, Ed: I. Gresser, Academic Press, 1982, pp. 47–94; M. Moore, Interferon and the Immune System, 2: Effect of IFN on the Immune System, Interferons: From Molecular Biology to Clinical Application, Eds: D. C. Burke and A. G. Morris, Cambridge Univ. Press, 1983, pp. 181–209; H. Smith-Johannsen, Y-T Hou, X-T Liu, and Y-H Tan, Chapter 6, Regulatory Control of Interferon Synthesis and Action, Interferons and Their Applications, Eds: P. E. Came and W. A. Carter, Springer Verlag, (Handbook of Experimental Pharmacology V. 71) 1984, pp. 101–135; J. L. Raylor, J. L. Sabram, and S. E. Grossberg, Chapter 9, The Cellular Effects of Interferon, Ibid. pp. 169–204; J. M. Zarling, Effects of Interferon and Its Inducers on Leukocytes and Their Immunologic Functions, Ibid. pp. 403–431; R. Ravel, The Interferon System in Man: Nature of the Interferon Molecules and Mode of Action, Antiviral Drugs and Interferon: The Molecular Basics of Their Activity, Ed: Y. Becker, Martinus Nijhoff Pub., 1984, pp. 357–433.

Further, "new" biological activities for exogenous and endogenous interferon are consistently being ascertained. K. Berg, M. Hokland, and I. Heron, Biological Activities of Pure HuIFN-Alpha Species, Interferon, Properties, Mode of Action, Production, Clinical Application, Eds: K. Munk and H., Kirchner, (Beitrage zur Onkologie V. 11) pp. 118–126; S. Pestka et al, The Specific Molecular Activities of Interferons Differe for Antiviral, Antiproliferative and Natural Killer Cell Activities, The Biology of the Interferon System, 1983, Eds: E. DeMaeyer and H. Schellekens, pp. 535–549; P. K. Weck and P. E. Came, Chapter 16, Comparative Biologic Activities of Human Interferons, Interferons and Their Applications, Eds: P. E. Came and W. A. Carter, Springer Verlag, (Handbook of Experimental Pharmacology V. 71) 1984, pp. 339–355.

Prior to the invention described and claimed in U.S. patent application Ser. No. 06/448,951, filed on Dec. 13, 1982, now U.S. Pat. No. 4,497,795, the disclosure of which is incorporated herein by reference, there had been no reports of the ability of interferon to regulate the appetite and efficiency of food utilization of warm-blooded vertebrates. That application discloses that interferon does have such activity.

One viral disease which has not been controlled, by interferon or other means, is bovine respiratory disease complex (BRDC). BRDC is an all-encompassing term describing an acute, contagious infection of cattle characterized by inflammation of the upper respiratory passages and trachea. BRDC leads to pneumonia with clinical signs of dyspnea, anorexia, fever, depression, mucopurulent nasal discharge and mucopurulent ocular discharge, all of which result in high morbidity and mortality. BRDC is a major cause of disease loss in beef cattle. The economic loss to cattlemen for treatment, weight loss, death loss, and culling is estimated to be $333,000,000 annually (National Cattlemen's Association, 1980).

When BRDC symptomology is observed in cattle after transport to feedlots or pastures, it is commonly called "shipping fever." On their way to the feedlot, calves are subjected to the stresses of intensive management techniques, transportation without food or water, and a variety of infectious agents. Upon arrival at the feedlot, processing exposes the calves to the additional stresses of weaning, castration, dehorning, branding, eartagging, worming, vaccination, and delousing. In many situations, calves are stressed still further by changes in diet and environmental factors.

The infectious agents to which calves entering the marketing system are exposed to include viruses (infectious bovine rhinotracheitis (IBR), parainfluenza type 3, bovine viral diarrhea, respiratory syncytical, adenoviruses, enteroviruses, rhinoviruses, parvoviruses, and reoviruses), bacteria (*Pasteurella hemolytica, Pasteurella multocida*, and *Hemophilus somnus*), mycoplasma (*M. dispar, M. bovirhinis, M. bovis*, and *M. arginini*), and Chlamydia.

The herpesvirus, IBR virus, is one of the infectious agents that is most commonly isolated by veterinary diagnostic laboratories in cases of BRDC. While some commercial vaccines for IBR are available, they have not been completely satisfactory in the past, partly because immunization of calves stressed by shipping can exacerbate the clinical signs of the disease. Also, some calves will not develop antibodies after vaccination, leaving them still susceptible to infection. Furthermore, many commercial vaccines are designed to provide protection no sooner than 14 days after vaccination, tracking the U.S. Department of Agriculture immunogenicity test. Because of the imperfections of the vaccination treatments used in the past and the enormous economic losses involved, a need exists for improved methods of preventing and treating bovine respiratory disease.

There is also a need for improved methods of regulating appetite and efficiency of feed utilization in warm-blooded vertebrates. In all the known previous interferon research, whether its goal was to assess antiviral, antiproliferative, or appetite regulating activity, the interferon dosages used have been generally high. Applicant has now made the surprising discovery that much lower dosages can produce superior effects.

SUMMARY OF THE INVENTION

Methods in accordance with the present invention utilize low dosages of interferon to achieve certain desirable biological effects in warm-blooded vertebrates. One method in accordance with the present invention which can increase the efficiency of food utilization in warm-blooded vertebrates comprises administering to a warm-blooded vertebrate a biologically active interferon in a dosage no greater than about 5 international units (IU)/lb of body weight per day. The presently preferred method is to administer human interferon alpha orally in a dosage between approximately 0.10 and 1.5 IU/lb of body weight per day. Treatment on three consecutive days is the preferred schedule, although different schedules can be used.

Methods in accordance with the present invention can also prevent and treat bovine respiratory disease complex. By administering a biologically active interferon to cattle in a dosage no greater than about 5 IU/lb of body weight per day, the appetite and feed utilization-related symptoms, as well as other symptoms of BRDC, can be ameliorated. These methods permit the effective treatment of shipping-stressed cattle, including cattle suffering from infectious bovine rhinotracheitis.

The present invention achieves its effects with doses of interferon which are much smaller than any known to have been used previously. In addition to the favorable biological activity, using smaller doses naturally makes these methods less expensive. Methods in accordance with the present invention are applicable to animal species such as bovine, porcine, caprine, ovine, avian, feline, canine, and equine animals, as well as humans.

The interferon administered can be of heterologous or homologous species origin. ("Heterologous species origin" means that the interferon has been derived from cells of a species other than that to which it is administered.)

The optimum dosage of interferon varies somewhat species to species, and probably animal to animal. Also, effects similar to those produced by a given daily dosage administered for a given number of days might be achieved by administering a slightly lower dosage for a slightly greater number of days, or a slightly higher dosage for a slightly smaller number of days. Along the same lines, if an animal has an infection that is causing it to secrete some interferon naturally, the dosage to be administered might be reduced somewhat to achieve the same biological effects.

DETAILED DESCRIPTION OF SPECIFIC EMBODIMENTS

Applicant's previous patent application, U.S. Ser. No. 448,951, filed on Dec. 13, 1982, discloses that the appetite of warm-blooded vertebrates can be regulated by a method comprising administering to the warm-blooded vertebrate a biologically active fraction of interferon in an amount effective to modulate the vertebrate's food intake or efficiency in utilizing food. The application discloses that interferon from any cell source may be used, as may genetically engineered interferon. Fibroblast interferon found in cells of bovine species origin is disclosed to be one suitable interferon, and oral administration to be the preferred route of treatment. The following description shows how such effects can be produced by using low-dosages of interferon.

The methods of the present invention can use interferons produced by methods known to those skilled in the art. One specific suitable method of preparing an interferon is described below.

EXAMPLE 1

Human interferon alpha can be prepared through the following procedure, commonly referred to as the Cantell procedure. The process begins with packs of human leukocytes, obtained in this case from the Gulf Coast Regional Blood Center, Houston, Tex. The buffy coats in these packs are pooled into centrifuge bottles, and then are diluted with 0.83% ammonium chloride. The mixture is incubated for 15 minutes with intermittent shaking, and is then centrifuged for 20 minutes at 2000 rpm. The supernatant is discarded, and the cell pellets are resuspended with a minimal volume of sterile phosphate buffered saline (PBS). The mixture is then diluted with ammonium chloride and centrifuged. The supernatant is again discarded, and the remaining cell pellets are resuspended with a minimal volume of a tissue culture medium such as Minimal Essential Medium (MEM), available from KC Biological. The cell concentration is determined with a Coulter counter.

Interferon induction takes place in glass or plastic bottles. The induction medium contains MEM, 75 mM Hepes (available from Calbiochem), 75 mM Tricine (available from Sigma Chemical Co.), human agamma serum (18 mg/ml), and gentamycin sulphate (from M.A. Bioproducts; 50 mcg/ml). The cells are added to the induction vessels at a final concentration of about 5 to 10 million cells per milliliter. The induction vessel is incubated in a 37° C. water bath, and interferon alpha is added as a primer.

After two hours, Sendai virus is added to the induction mixture. This causes alpha interferon to be produced in the supernatant by the leukocytes. After a 12–18 hour incubation time, the induction mixture is centrifuged. The cells are discarded, and the supernatant is then purified.

The crude interferon is chilled to 10° C. or below in an ice bath. Five molar potassium thiocyanate is added to obtain a final concentration of 0.5M. This solution is stirred for 15 minutes, and then its pH is lowered to 3.3 by adding hydrochloric acid. The mixture is then centrifuged at 2800 rpm for 30 minutes, and the supernatant is discarded.

The pellets are then resuspended in 95% ethanol and are stirred for 15 minutes. This suspension is centrifuged at 2800 rpm for 20 minutes, and the pellets are discarded. The pH of the supernatant is then adjusted to 5.8 with sodium hydroxide. The mixture is stirred for 10 minutes, and then centrifuged at 2800 rpm for 20 minutes. The pellets are discarded. The pH of the supernatant is then adjusted to 8 with sodium hydroxide. This solution is stirred for 10 minutes, followed by centrifugation at 2800 rpm for 20 minutes. The supernatant is discarded, and the pellets are resuspended with 0.5M potassium thiocyanate in a 0.1M sodium phosphate buffer. This suspension is stirred at 4° C.

Next, the suspension is centrifuged at 2800 rpm for 20 minutes, and the pellets are discarded. The pH of the supernatant is adjusted to 5.3 with hydrochloric acid. After stirring for 10 minutes and centrifugation, the pH of the supernatant is adjusted to 2.8 with hydrochloric acid, followed by further stirring for 20 minutes. This mixture is centrifuged at 2800 rpm, and the resulting pellet is purified human interferon alpha.

The pellet is resuspended with 0.5M potassium thiocyanate in 0.1M sodium phosphate buffer, having a pH of 8.0. It is then dialyzed against PBS at 4° C., with two changes of PBS. This mixture is then centrifuged and the precipitate is discarded. The remaining purified alpha interferon is sterilized by filtration through a 0.2 micron filter.

A human interferon alpha is produced in accordance with this procedure by Immuno Modulators Laboratories, Inc., Stafford, Tex., and sold under the trademark Agriferon®-C.

Other procedures known to those skilled in the art are available for making interferons, such as human interferon alpha and human interferon gamma. For example, U.S. Pat. Nos. 4,376,821 and 4,460,685 disclose methods of making human interferon gamma. A method of making bovine fibroblast interferon is disclosed in Applicant's prior patent application cited above.

EXAMPLE 2

This experiment demonstrates effective routes of administration and dosages of human interferon alpha as an aid in the prevention and/or treatment of IBR virus infection in cattle. Thirty-six beef calves 9 to 12 months old, weighing 436 to 684 pounds, were obtained from the Texas Agricultural Experiment Station, Amarillo, Tex. The calves were divided into three weight groups and randomly placed in treatment groups. Treatments of human interferon alpha were administered orally (OS), intranasally (IN), or intravenously (IV). Table 1 shows the number of calves for each route of administration and dosage.

TABLE 1

Number of Calves Treated by Various Routes of Administration and Dosages of Interferon

| Dosage | Routes | | |
|---|---|---|---|
| (IU/lb) | OS | IN | IV |
| 1953.0 | — | 3 | — |
| 1938.0 | 3 | — | — |
| 953.7 | — | — | 3 |
| 201.1 | 3 | — | — |
| 197.7 | — | 3 | — |
| 94.9 | — | — | 3 |
| 20.0 | — | 4 | — |
| 18.0 | 3 | — | — |

TABLE 1-continued

Number of Calves Treated by Various Routes of Administration and Dosages of Interferon

| Dosage | Routes | | |
|---|---|---|---|
| (IU/lb) | OS | IN | IV |
| 10.3 | — | — | 3 |
| 0 | 2 | 2 | 4 |

Control calves were given MEM as a placebo. The interferon was administered daily for three consecutive days starting at the time of inoculation with a virulent IBR virus (Cooper strain) obtained from National Animal Disease Laboratory, Ames, Iowa. The challenge dose of this virus as $10^{6.6}$ TCID$_{50}$ per calf. The calves were seronegative to IBR virus at the time of virus challenge.

IBR virus inoculations were given intranasally by syringe in a 2 ml dose per nostril. Body weight and rectal temperatures were recorded periodically and blood for serum interferon and serum antibody determinations were collected from each calf. Nasal swab samples were taken for viral isolation, and nasal tampons were used to obtain nasal secretion samples for interferon assays.

The results of the tests are shown below. Table 2 shows the rectal temperatures of the calves at various times after inoculation; Table 3 shows the IBR virus titer in the calves' nasal secretions; Table 4 shows the interferon titer in the calves' nasal secretions; Table 5 shows the serum antibody titers to IBR virus; Table 6 shows the feed consumption of the calves (measured using pinpointers from UIS Inc., Cookeville, Tenn.); Table 7 shows performance data for the calves; and Table 8 shows mortality and performance data.

TABLE 2

| | | | Rectal Temperatures (°F.) | | | | | | | |
|---|---|---|---|---|---|---|---|---|---|---|
| | Calves | Dosage | Days After IBR Virus Inoculation | | | | | | | |
| Route | Treated | (IU/lb) | 0 | 2 | 3 | 5 | 6 | 7 | 9 | 14 |
| IN | 3 | 1953.0 | 102.8 | 102.4 | 105.7 | 104.9 | 105.5 | 105.2 | 103.9 | 102.3 |
| IN | 3 | 197.7 | 102.1 | 104.1 | 106.3 | 104.9 | 105.6 | 104.4 | 104.4 | 102.8 |
| IN | 4 | 20.0 | 103.4 | 104.6 | 105.4 | 105.2 | 105.2 | 104.5 | 104.4 | 102.4 |
| OS | 3 | 1928.0 | 102.7 | 102.8 | 105.6 | 106.0 | 106.1 | 105.0 | 104.2 | 102.0 |
| OS | 3 | 201.1 | 102.4 | 103.7 | 104.4 | 105.3 | 105.8 | 104.5 | 103.3 | 101.6 |
| OS | 3 | 18.0 | 102.9 | 104.2 | 104.5 | 105.3 | 106.3 | 104.5 | 103.4 | 101.4 |
| OS-IN* | 4 | 0.0 | 102.6 | 104.0 | 104.8 | 105.7 | 105.0 | 104.2 | 102.8 | 102.0 |
| IV | 3 | 953.7 | 102.8 | 103.3 | 106.0 | 105.8 | 105.7 | 104.4 | 104.3 | 102.1 |
| IV | 3 | 94.9 | 102.8 | 104.4 | 104.8 | 105.3 | 105.4 | 104.8 | 104.1 | 100.8 |
| IV | 3 | 10.3 | 102.6 | 104.1 | 105.2 | 106.1 | 105.9 | 105.1 | 104.3 | 103.2 |
| IV | 4 | 0.0 | 102.3 | 103.9 | 105.3 | 106.2 | 106.2 | 105.5 | 104.6 | 102.3 |

*Placebo was given orally to 2 calves and intranasally to 2 calves.

TABLE 3

| | | | Geometric Mean Titer of IBR Virus in Nasal Secretions | | | | | |
|---|---|---|---|---|---|---|---|---|
| | Calves | Dosage | Days After IBR Virus Inoculation | | | | | |
| Route | Treated | (IU/lb) | 0 | 2 | 3 | 5 | 9 | 14 |
| IN | 3 | 1953.0 | 0 | 2,996,000 | 2,125,300 | 1,090,300 | 1,142 | 0 |
| IN | 3 | 197.7 | 0 | 244,900 | 201,700 | 575,300 | 4,191 | 0 |

TABLE 3-continued

Geometric Mean Titer of IBR Virus in Nasal Secretions

| Route | Calves Treated | Dosage (IU/lb) | \multicolumn{6}{c}{Days After IBR Virus Inoculation} | | | | | |
|---|---|---|---|---|---|---|---|---|
| | | | 0 | 2 | 3 | 5 | 9 | 14 |
| IN | 4 | 20.0 | 0 | 357,500 | 358,300 | 813,000 | 1,123 | 0 |
| OS | 3 | 1938.0 | 0 | 1,129,200 | 889,600 | 660,400 | 39,300 | 0 |
| OS | 3 | 201.1 | 0 | 1,153,800 | 405,900 | 279,500 | 1,940 | 0 |
| OS | 3 | 18.0 | 0 | 163,900 | 342,100 | 1,406,800 | 2,844 | 0 |
| OS-IN* | 4 | 0.0 | 0 | 535,722 | 414,925 | 1,305,884 | 276 | 0 |
| IV | 3 | 953.7 | 0 | 338,800 | 756,000 | 526,100 | 2,303 | 0 |
| IV | 3 | 94.9 | 0 | 1,248,000 | 607,300 | 1,788,400 | 4,066 | 0 |
| IV | 3 | 10.3 | 0 | 560,800 | 726,800 | 853,400 | 26,000 | 0 |
| IV | 4 | 0.0 | 0 | 1,172,872 | 834,018 | 485,911 | 2,759 | 0 |

*Placebo was given orally to 2 calves and intranasally to 2 calves.

TABLE 4

Geometric Mean Titer of Interferon in Nasal Secretions

| Route | Calves Treated | Dosage (IU/lb) | \multicolumn{6}{c}{Days After IBR Virus Inoculation} | | | | | |
|---|---|---|---|---|---|---|---|---|
| | | | 0 | 2 | 3 | 5 | 9 | 14 |
| IN | 3 | 1953.0 | 0 | 605 | 2,378 | 1,241 | 0 | 0 |
| IN | 3 | 197.7 | 0 | 236 | 550 | 1,030 | 26 | 0 |
| IN | 4 | 20.0 | 0 | 541 | 767 | 1,012 | 0 | 0 |
| OS | 3 | 1938.0 | 0 | 318 | 2,540 | 627 | 43 | 0 |
| OS | 3 | 201.1 | 0 | 270 | 1,370 | 3,003 | 0 | 0 |
| OS | 3 | 18.0 | 0 | 652 | 466 | 876 | 0 | 0 |
| OS-IN* | 4 | 0.0 | 0 | 786 | 1,011 | 481 | 0 | 0 |
| IV | 3 | 953.7 | 0 | 157 | 1,481 | 959 | 0 | 0 |
| IV | 3 | 94.9 | 0 | 695 | 3,842 | 727 | 0 | 0 |
| IV | 3 | 10.3 | 0 | 429 | 1,542 | 548 | 0 | 0 |
| IV | 4 | 0.0 | 0 | 251 | 3,559 | 707 | 24 | 0 |

*Placebo was given orally to 2 calves and intranasally to 2 calves.

TABLE 5

Geometric Mean Serum Antibody Titers to IBR Virus After Challenge

| Route | Calves Treated | Dosage (IU/lb) | \multicolumn{3}{c}{Days After IBR Virus Inoculation} | | |
|---|---|---|---|---|---|
| | | | 0 | 14 | 27 |
| IN | 3 | 1953.0 | <4 | 10.1 | 80.6 |
| IN | 3 | 197.7 | <4 | 50.8 | 101.6 |
| IN | 4 | 20.0 | <4 | 16.0 | 90.5 |
| OS | 3 | 1938.0 | <4 | 12.7 | 64.0 |
| OS | 3 | 201.1 | <4 | 6.3 | 101.6 |
| OS | 3 | 18.0 | <4 | 6.3 | 161.3 |
| OS-IN* | 4 | 0.0 | <4 | 19.0 | 107.6 |
| IV | 3 | 953.7 | <4 | 12.7 | 128.0 |
| IV | 3 | 94.9 | <4 | 64.0 | 64.0 |
| IV | 3 | 10.3 | <4 | 32.0 | 64.0 |
| IV | 4 | 0.0 | <4 | 16.0 | 152.2 |

*Placebo was given orally to 2 calves and intranasally to 2 calves.

TABLE 6

Feed Consumption (Daily Consumption as Percentage of Body Weight)

| Route | Calves Treated | Dosage (IU/lb) | Prior** | \multicolumn{9}{c}{Days After IBR Virus Inoculation} | | | | | | | | |
|---|---|---|---|---|---|---|---|---|---|---|---|---|
| | | | | 0 | 2 | 3 | 5 | 6 | 7 | 9 | 11 | 13 |
| IN | 3 | 1953.0 | 3.56 | 2.96 | 2.85 | 1.51 | 0.92 | 0.81 | 0.82 | 2.67 | 2.41 | 3.52 |
| IN | 3 | 197.7 | 3.28 | 2.59 | 1.30 | 0.45 | 0.89 | 0.74 | 1.29 | 1.55 | 2.62 | 3.34 |
| IN | 4 | 20.0 | 3.49 | 2.92 | 1.75 | 1.66 | 1.29 | 1.65 | 1.89 | 2.38 | 3.23 | 3.78 |
| OS | 3 | 1938.0 | 3.38 | 2.97 | 3.19 | 1.39 | 0.18 | 0.04 | 0.34 | 0.56 | 1.46 | 2.52 |
| OS | 3 | 201.1 | 3.29 | 3.99 | 2.21 | 1.60 | 1.55 | 0.88 | 1.90 | 2.90 | 3.26 | 3.55 |
| OS | 3 | 18.0 | 3.13 | 3.31 | 2.71 | 1.37 | 1.39 | 1.70 | 2.00 | 3.17 | 2.81 | 3.58 |
| OS-IN* | 4 | 0.0 | 3.23 | 3.19 | 2.56 | 1.00 | 1.26 | 1.64 | 1.76 | 2.73 | 4.08 | 4.82 |
| IV | 3 | 953.7 | 3.10 | 3.43 | 1.75 | 0.89 | 0.82 | 0.48 | 0.80 | 1.88 | 2.64 | 2.15 |
| IV | 3 | 94.9 | 2.75 | 2.47 | 1.90 | 1.02 | 0.60 | 0.40 | 0.72 | 1.78 | 2.08 | 2.82 |
| IV | 3 | 10.3 | 3.13 | 3.44 | 2.40 | 0.96 | 0.69 | 0.42 | 0.18 | 0.99 | 1.53 | 2.13 |
| IV | 4 | 0.0 | 3.26 | 3.03 | 1.93 | 1.08 | 0.74 | 0.85 | 0.84 | 1.52 | 1.97 | 2.95 |

*Placebo was given orally to 2 calves and intranasally to 2 calves.
**Consumption (prior to experiment) as a percentage of body weight.

TABLE 7

Weight Change After 14 Days

| Route | Calves Treated | Dosage (IU/lb) | 14 Day Gain (lb) |
|---|---|---|---|
| IN | 3 | 1953.0 | −5.3 |
| IN | 3 | 197.7 | −29.4 |
| IN | 4 | 20.0 | −1.8 |
| OS | 3 | 1938.0 | −56.0 |
| OS | 3 | 201.1 | −15.6 |
| OS | 3 | 18.0 | +5.7 |
| OS-IN* | 4 | 0.0 | −6.0 |
| IV | 3 | 953.7 | −36.3 |
| IV | 3 | 94.9 | −58.7 |
| IV | 3 | 10.3 | −35.7 |
| IV | 4 | 0.0 | −41.3 |

*Placebo was given orally to 2 calves and intranasally to 2 calves.

TABLE 8

Mortality and Weight Change After 27 Days

| Route | Calves Treated | Dosage (IU/lb) | No. Dead Calves | Daily Gain (lbs) (27 days) |
|---|---|---|---|---|
| IN | 3 | 1953.0 | 0 | 0.28 |
| IN | 3 | 197.7 | 0 | 0.34 |
| IN | 4 | 20.0 | 0 | 0.70 |
| OS | 3 | 1938.0 | 1 | 0.74 |
| OS | 3 | 201.1 | 0 | 0.22 |
| OS | 3 | 18.0 | 0 | 1.74 |
| OS-IN* | 4 | 0.0 | 0 | 0.54 |
| IV | 3 | 953.7 | 1 | 1.19 |
| IV | 3 | 94.9 | 1 | 0.74 |
| IV | 3 | 10.3 | 1 | 1.24 |
| IV | 4 | 0.0 | 0 | −0.47 |

*Placebo was given orally to 2 calves and intranasally to 2 calves.

The calves showed an onset of fever greater than 104° F. by the third day after inoculation, and returned to normal temperature by the 14th day, indicative of a successful viral challenge. At the highest dose of interferon, when given orally or intranasally, the onset of the fever was delayed one day.

Concomitant with this rise in temperature was an increase in the geometric mean titer of IBR virus, as shown in Table 3. When the interferon was given intranasally at the highest dose, a significant increase in the geometric mean titer occurred on day 3 compared to the other intranasal doses. However, when the interferon was given orally, the highest dose was significantly different at day 9 compared to the other oral doses. This may demonstrate an overdose of interferon resulting in an increase in virus excretion. Peak IBR virus excretion occurred latest in the lowest oral dosage group. All three orally treated groups were excreting more virus than controls by the 9th day, but only the highest oral dosage group was significantly higher than the controls. Peak IBR virus excretion occurred on the 5th day in the intermediate and low intranasal dose groups, but on the second day in the highest intranasal dosage group. More virus was excreted in the highest oral dosage group. With both the oral and intranasal routes, the lowest doses resulted in less IBR virus excretion on the second and third days, but more during later stages of the infection. Observations of calves given the intranasal dose indicated that most of the applied dosage was swallowed, and some was expelled from the nasal passage, so the intranasal route appeared to be an inefficient method.

By the fourteenth day after inoculation, IBR virus antibody was detected in all the calves. Antibody to IBR virus was not delayed by any dosage or route of interferon.

Calves given human interferon alpha at the highest oral dose consumed significantly less feed as a percentage of body weight on the fifth, sixth and ninth day than did the other oral dosage groups. The significantly decreased feed intake for the highest oral dose, accompanied by no differences between the lowest oral dose and controls, indicates that high doses of interferon could be less desirable for appetite regulation purposes than low doses.

While all the other groups lost weight, the calves given the lowest oral dose gained weight during the fourteen day period of viral infection. The highest oral dose group had significantly greater weight loss by the fourteenth day than the lowest oral dose group or than controls. Although four of the calves died of bacterial pneumonia, no pathology was observed that could be attributed to the administration of the interferon.

In summary, human interferon alpha administered orally at the lowest dose (18.0 IU/lb) appeared to be the most beneficial route and dosage. More interferon appeared not to be better than less interferon.

EXAMPLE 3

This experiment demonstrates the effective oral dosage of interferon to provide an antiviral effect against virulent IBR virus in a challenge model. Forty beef calves nine to twelve months of age, weighing 430 to 749 pounds, were obtained from the Texas Agricultural Experiment Station. The calves were allotted to five equal weight groups of eight calves each, and each group was randomly assigned to treatments. The treatment groups were administered roughly 0, 0.01, 0.10, 1.0 or 10.0 units of human interferon alpha per pound of body weight. The 0 treatment group was given MEM as a placebo.

Beginning two days prior to challenge to virulent IBR virus, the calves were given single, daily oral doses of interferon (or placebo) for three days, with the final dose being on the day of inoculation. IBR virus inoculations were given by syringe in a two milliliter dose per nostril ($10^{6.6}$ $TCID_{50}$ per calf). All calves included in the study were seronegative to IBR virus at the time of inoculation. Seven calves were removed from the study because two of them developed IBR virus antibody by the day of inoculation, and five would not consume feed from the feed consumption measuring device.

Table 9 shows the number of calves given each dosage level of interferon; Table 10 shows the IBR virus titers in the calves' nasal secretions; and Table 11 shows a summary of the results. The feed/gain ratio in Table 11 represents pounds of feed consumed divided by pounds of gain over the first 11 days.

TABLE 9

Dosages of Interferon

| Group | No. of Calves | Units of HuIFN-A per/lb of Body Weight |
|---|---|---|
| A | 6 | 0 |
| B | 8 | 0.01 |
| C | 8 | 0.08–0.12 |
| D | 7 | 0.94–1.3 |
| E | 4 | 8.70–13.00 |

TABLE 10

Geometric Mean Titer (GMT)
of IBR Virus in Nasal Secretions
(Plaque Forming Units)

| Group | No. of Calves | Treatment (IU/lb) | Days After IBR Virus Inoculation | | | | |
|---|---|---|---|---|---|---|---|
| | | | 0 | 3 | 7 | 11 | 14 |
| A | 6 | 0 | 0 | 193,000 | 86,000 | 1.3 | 0 |
| B | 8 | 0.01 | 0 | 342,000 | 142,000 | 3.2 | 0 |
| C | 8 | 0.08–0.12 | 0 | 22,000 | 218,000 | 7.7 | 0 |
| D | 7 | 0.94–1.30 | 0 | 26,000 | 29,000 | 1.5 | 0 |
| E | 4 | 8.7–13.00 | 0 | 95,000 | 146,000 | 1.2 | 0 |

TABLE 11

Summary of Results

| Variable | Treatment (IU/lb) | | | | |
|---|---|---|---|---|---|
| | 0 | 0.01 | 0.08–0.12 | 0.94–1.30 | 8.7–13.00 |
| Duration of fever >104° F. (days) | 5.0 | 3.9 | 3.9 | 3.0 | 4.2 |
| Average peak fever (°F.) | 106.1 | 105.8 | 105.6 | 105.3 | 106.6 |
| Maximum weight loss during infection (lb) | 38.7 | 44.8 | 45.0 | 23.9 | 52.0 |
| Average daily gain at 11 days (lb) | −0.4 | 1.4 | −1.1 | 2.2 | 0.2 |
| Average daily gain at 31 days (lb) | 1.6 | 1.6 | 1.5 | 2.1 | 1.6 |
| GMT IBR virus (× 1,000) | | | | | |
| day 3 | 193.0 | 342.0 | 22.0 | 26.0 | 95.0 |
| day 7 | 86.0 | 142.0 | 218.0 | 29.0 | 146.0 |
| Feed/gain ratio for first 11 days | negative | 10.28 | negative | 6.88 | 79.89 |

Calves given approximately 1.0 units per pound of body weight (Group D) had the shortest duration of fever and the lowest peak fever of all the groups. The highest interferon dosage was significantly detrimental, as indicated by higher fever and lower gain. The antiviral protection of the Group D dosage, 0.94 to 1.30 units per pound, is evident in Table 10. Three days after virus inoculation, the Group D calves were excreting significantly less IBR virus than controls (26,000 plaque forming units vs. 193,000 PFU). At seven days after virus inoculation, the Group D calves were still excreting less virus (29,000 PFU vs. 86,000 PFU), although the difference was not significant. All calves failed to excrete virus on the fourteenth day after inoculation.

Most calves in all the groups lost weight after challenge with the IBR virus, then regained weight throughout the duration of the study. The Group D calves had the lowest weight loss during infection and the greatest weight gain at the end of the study, as shown in Table 11. Interferon dosage had a significant negative correlation with the weight loss which occurred after interferon administration and virus inoculation for Groups A through D.

This confirms the findings of Example 2 and further clarifies that the most effective dose of human interferon alpha is an extremely low oral dose. The dosage of approximately 1.0 IU/lb of body weight resulted in decreased virus excretion, the shortest fever duration, the smallest weight loss, the lowest peak fever, the greatest average daily weight gain, and the best feed conversion.

EXAMPLE 4

This test demonstrates the practicality and economic benefit of administering human interferon alpha to feeder calves undergoing a mixed viral infection in a shipping fever transport model. The calves were handled as closely as possible to what they would experience in an actual marketing system. Forty beef calves were purchased from an order buyer in Tennessee in a manner similar to that used by a feedlot operator, and were trucked to Amarillo, Tex. (1,180 miles) in 24 hours without access to food or water. The calves were from nine to twelve months old, weighed 405–545 pounds, and had been obtained from various auction markets in the southeastern United States by the order buyer.

The calves were allotted to three treatment groups, eartagged for identification and randomly assigned to treatment groups: 10 calves were given one oral dose of 1.0 to 1.5 units per lb; 10 calves were given two oral doses at the same dosage on consecutive days; and twenty calves served as untreated controls. The last interferon dose was given two days before shipment.

On arrival at the feedlot in Amarillo, the calves were weighed and rectal temperatures recorded. Calves were then given access to feed and water. The next day they were processed, reweighed and temperatures recorded. The processing consisted of worming, four-way clostridial bacterin,. delousing with an external insecticide, an injection of vitamins A and D, and a bleeding for serology.

A natural shipping fever outbreak occurred, and three calves died of pneumonia: one control and two that were given one dose of interferon.

Thirty-seven days after processing, the ten calves given two doses of interferon before shipment had a significantly greater weight gain than the control calves. The calves given one dose gained better than the controls, but not as well as the two-dose calves. Also, the calves given interferon converted feed into weight gain more efficiently than controls. The benefits of the treatment are summarized in Table 12.

TABLE 12

Benefits of HuIFN-A On
Shipping Stressed Feeder Calves

| No. of Calves | No. of Days | Daily Dosage (IU/lb) | Number Survived | Processing Weight (lb) | Average Gain Over 37 Days (lb) | Feed/Gain Ratio |
|---|---|---|---|---|---|---|
| 20 | 0 | 0 | 19 | 438.2 | 48.5 | 16.6 |
| 10 | 1 | 1.0–1.5 | 8 | 430.8 | 92.1 | 6.0 |
| 10 | 2 | 1.0–1.5 | 10 | 443.8 | 112.3 | 5.9 |

EXAMPLE 5

Forty feeder calves were randomly assigned to four treatment groups of 10 calves each. All the calves were seronegative to IBR virus. The calves were given placebo or interferon (human alpha) orally at three different dosages (0.05, 0.5, or 5.0 IU/lb of body weight). A dose of interferon or placebo was given on the day before, on the day after, and on the day of IBR virus inoculation. Each calf was given $10^3$ plaque forming units (PFU) of IBR virus/nostril.

Tables 13 through 18 show the results of this test.

TABLE 13

Number of Calves with a Temperature of at Least 104° F.

| Treatment Group | Days After IBR Virus | | | | | | | | | | | | | | | |
|---|---|---|---|---|---|---|---|---|---|---|---|---|---|---|---|---|
|  | −1 | 0 | 1 | 2–4 | 5 | 6 | 7 | 8 | 9 | 10 | 14 | 18 | 19 | 23 | 25 | Total |
| Control | 1 | 0 | 2 | 1 | 0 | 1 | 1 | 2 | 0 | 0 | 3 | 4 | 1 | 2 | 0 | 18 |
| 0.05 IU/lb | 1 | 1 | 1 | 0 | 2 | 3 | 4 | 4 | 3 | 4 | 2 | 2 | 0 | 2 | 0 | 29 |
| 0.5 IU/lb | 0 | 0 | 1 | 0 | 2 | 5 | 7 | 6 | 3 | 1 | 0 | 0 | 0 | 0 | 0 | 25 |
| 5.0 IU/lb | 1 | 1 | 1 | 1 | 3 | 2 | 6 | 4 | 1 | 0 | 1 | 2 | 0 | 2 | 0 | 25 |

TABLE 14

Average Daily Gains at 14 Days After Inoculation

| Treatment Group | Average Daily Gains from Day | | |
|---|---|---|---|
|  | −3 | −1 | 0 |
| Control | 0.38 | 1.35 | 1.29 |
| 0.05 IU/lb | −0.24 | 1.05 | 0.89 |
| 0.5 IU/lb | 1.43 | 2.99 | 2.74 |
| 5.0 IU/lb | −0.08 | 1.69 | 1.54 |

TABLE 15

Feed Consumption and Gain for 14 Days After Inoculation

| Treatment Group | Average Daily Gain (lb/day) | Average Daily Consumption (lb/day) | Feed/Gain |
|---|---|---|---|
| Control | 1.29 | 16.1 | 12.5 |
| 0.05 IU/lb | 0.89 | 15.3 | 17.2 |
| 0.5 IU/lb | 2.74 | 14.7 | 5.4 |
| 5.0 IU/lb | 1.54 | 15.0 | 9.6 |

TABLE 16

Feed Consumption and Gain for 27 Days After Inoculation

| Treatment Group | Gain (lbs) | Average Daily Gain (lb/day) | Estimated Average Daily Consumption (lb/day) | Feed/Gain |
|---|---|---|---|---|
| Control | 500 | 1.85 | 16.4 | 8.9 |
| 0.05 IU/lb | 534 | 1.98 | 15.2 | 7.7 |
| 0.5 IU/lb | 634 | 2.35 | 14.9 | 6.4 |
| 5.0 IU/lb | 586 | 2.10 | 14.9 | 7.1 |

TABLE 17

Geometric Mean Serum Antibody Titers (log base 2) to IBR Virus

| Treatment Group | Days After Virus | | |
|---|---|---|---|
|  | 0 | 14 | 25 |
| Control | 0 | 1.9 | 29.8 |
| 0.05 IU/lb | 0 | 3.7 | 27.9 |
| 0.5 IU/lb | 0 | 8.8 | 24.3 |
| 5.0 IU/lb | 0 | 4.6 | 21.1 |

TABLE 18

Geometric Mean Titers of IBR Virus (Plaque Forming Units) in Nasal Secretions

| Treatment Group | Days After Inoculation | | | | |
|---|---|---|---|---|---|
|  | 0 | 3 | 7 | 10 | 14 |
| Control | 0 | 2 | 204 | 6,310 | 12,078 |
| 0.05 IU/lb | 0 | 21 | 3,396 | 174,582 | 298 |
| 0.5 IU/lb | 0 | 221 | 20,749 | 20,184 | 7 |
| 5.0 IU/lb | 0 | 71 | 4,130 | 43,451 | 132 |

The rectal temperatures of the cattle did not differ significantly among the four treatment groups after inoculation with the IBR virus. However, as Table 13 shows, more calves given the 0.5 IU/lb dosage had fever of at least 104° F. in the five to nine days after inoculation period.

Tables 14 and 15 show that the calves given the 0.5 IU/lb dose gained significantly more than controls during the first 14 days and exhibited improved feed conversion. The results for gain and feed-to-gain ratio at 27 days favored all three of the treated groups over the controls, but not significantly so, as shown in Table 16.

Antibodies to IBR virus were produced in all the groups, and Table 17 shows that the production occurred significantly faster in the group treated with 0.5 IU/lb. Nasal excretion of IBR virus also occurred sooner in the 0.5 IU/lb treatment group, as shown in Table 18. Significantly more virus was excreted by the 0.5 IU/lb group compared to controls at three days (221 PFU vs. 2 PFU) and seven days (20,749 PFU vs. 204 PFU) after virus inoculation. By 14 days, however, controls were excreting more virus than any interferon-treated group (12,078 PFU vs. 298 or 7 or 132 PFU). These data indicate that the initial viral infection may have been intensified and shortened in interferon-treated calves, resulting in faster recovery and better performance.

In summary, human interferon alpha administered orally at 0.5 IU/lb of body weight significantly stimulated antibody development, improved weight gain at 14 days after IBR virus inoculation, and increased IBR virus excretion at three and seven days, but decreased virus excretion at 14 days after inoculation. This dosage improved the efficiency of feed utilization during the first 14 days.

The foregoing description has been directed to particular embodiments of the invention in accordance with the requirements of the Patent Statutes for the purposes of illustration and explanation. It will be apparent, however, to those skilled in this art that many modifications and changes in the materials and methods set forth will be possible without departing from the scope and spirit of the invention. It is intended that the following claims be interpreted to embrace all such modifications and changes.

What is claimed is:

1. In a method for administering interferon orally to a warm-blooded vertebrate whereby ingested interferon is exposed to the digestive conditions of the vertebrate's digestive tract, the improvement which comprises administering interferon orally in solution at a unit dosage of about 0.1 to about 1.5 IU/lb of body weight of the vertebrate.

2. The improvement of claim 1 wherein said biologically active interferon is alpha interferon or beta interferon.

3. The improvement of claim 1 wherein the biologically active interferon is human alpha interferon.

4. The improvement of claim 3 wherein the human alpha interferon is administered in a sterile aqueous solution.

5. In a method for treating a warm-blooded vertebrate to stimulate antiviral, antiproliferative and immunomodulatory responses by oral administration of interferon whereby ingested interferon is subjected to the digestive conditions of the digestive tract of the warm-blooded vertebrate, the improvement which comprises administering the interferon orally in solution at about 0.1 to about 1.5 IU/lb of body weight per dose.

6. The improvement of claim 5 wherein said biologically active interferon is alpha interferon or beta interferon.

7. The improvement of claim 5 wherein the biologically active interferon is human alpha interferon.

8. The improvement of claim 7 wherein the human alpha interferon is administered in a sterile aqueous solution.

* * * * *